US010166345B2

(12) United States Patent
Erickson et al.

(10) Patent No.: US 10,166,345 B2
(45) Date of Patent: *Jan. 1, 2019

(54) SAFETY SYRINGE AND NEEDLE SHIELD

(71) Applicant: ULTIMED, INC., Exclesior, MN (US)

(72) Inventors: Thomas E. Erickson, Crosslake, MN (US); James J. Erickson, Mound, MN (US); Thomas Sauro, Rosemount, MN (US)

(73) Assignee: ULTIMED, INC., Exclesior, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/237,798

(22) Filed: Aug. 16, 2016

(65) Prior Publication Data

US 2017/0157335 A1 Jun. 8, 2017

Related U.S. Application Data

(63) Continuation of application No. 13/451,212, filed on Apr. 19, 2012, now Pat. No. 9,415,172.

(51) Int. Cl.
*A61M 5/32* (2006.01)
*A61M 5/31* (2006.01)

(52) U.S. Cl.
CPC ........ *A61M 5/3245* (2013.01); *A61M 5/3275* (2013.01); *A61M 2005/3114* (2013.01); *A61M 2005/3126* (2013.01); *A61M 2005/3253* (2013.01)

(58) Field of Classification Search
CPC .. A61M 2005/3114; A61M 2005/3253; A61M 5/3245; A61M 5/3275; A61M 2005/3126; A61M 5/3243
See application file for complete search history.

(56) References Cited

U.S. PATENT DOCUMENTS

| 4,027,669 | A | 6/1977 | Johnston et al. |
| 5,053,018 | A | 10/1991 | Talonn et al. |
| 5,088,988 | A | 2/1992 | Talonn et al. |
| 5,217,437 | A | 6/1993 | Talonn et al. |
| 5,312,370 | A | 5/1994 | Talonn et al. |
| 5,314,414 | A | 5/1994 | Hake et al. |
| 5,328,485 | A | 7/1994 | Moreno et al. |
| 5,338,303 | A | 8/1994 | King et al. |
| 5,403,287 | A | 4/1995 | Talonn et al. |
| 6,203,529 | B1 | 3/2001 | Gabriel et al. |

(Continued)

FOREIGN PATENT DOCUMENTS

| CA | 1105794 A | 7/1981 |
| EP | 0557511 A1 | 9/1993 |

(Continued)

*Primary Examiner* — Brandy S Lee
(74) *Attorney, Agent, or Firm* — Seager, Tufte & Wickhem LLP

(57) ABSTRACT

The disclosure pertains to a safety syringe having a retractable needle shield which is capable of being retracted to expose the needle for use; being advanced to a needle shielding position; and, if desired, of being removed from the syringe with the shielded needle safely contained within the retractable needle shield via a frangible segment between the syringe barrel and the needle/needle shield components. The disclosure further pertains to a method of using the safety syringe having a retractable needle shield.

17 Claims, 8 Drawing Sheets

(56) References Cited

U.S. PATENT DOCUMENTS

| | | | |
|---|---|---|---|
| 6,656,163 | B1 | 12/2003 | Marshall et al. |
| 9,415,172 | B2 * | 8/2016 | Erickson ............. A61M 5/3243 |
| 2007/0078406 | A1 | 4/2007 | Lee |
| 2007/0197966 | A1 | 8/2007 | Lee et al. |
| 2007/0197967 | A1 | 8/2007 | Lee et al. |

FOREIGN PATENT DOCUMENTS

| | | |
|---|---|---|
| GB | 2271934 A | 5/1994 |
| JP | 200084079 A | 3/2000 |
| JP | 2003199751 A | 7/2003 |

\* cited by examiner

SAFETY SYRINGE AND NEEDLE SHIELD

RELATED APPLICATIONS

This applications is a continuation of U.S. application Ser. No. 13/451,212, filed Apr. 19, 2012, now U.S. Pat. No. 9,415,172.

BACKGROUND

This disclosure relates to syringes and, in particular, to a hypodermic syringe having a retractable needle guard for the purpose of preventing accidental needle sticks.

Most syringes used today for medical or laboratory purposes are sold as disposable items intended to be used only once. Disposal of such syringes has posed a safety hazard for the individuals who use the syringes as well as for those who dispose of them. With the onset of AIDS, the concern for infection due to accidental needle sticks from used syringes has increased and a number of different devices have been proposed to minimize the possibility of spreading infectious disease due to accidents of this type.

One approach to this problem is to provide a retractable shield which, after the syringe has been used, can be pulled to an extended position where it covers the needle, making it difficult for an individual to accidentally contact the needle. A common feature of such constructions is that when the shield is pulled to its extended position, it is locked so that it cannot be retracted (thus exposing the needle) except by application of extraordinary force.

A number of such constructions have been proposed to satisfy the general requirement that the needle be permanently covered after the syringe has been used. Some of these constructions involve twist-to-lock mechanisms and, in others, locking occurs automatically when the shield is fully extended. These known devices satisfy many of the functional requirements of a needle shield and require, in most cases, modification of the standard syringe construction.

Those devices which lock in response to axial movement to the extended position, (i.e., without any rotation) have certain inherent drawbacks that result primarily from the requirement that substantial force be exerted axially to lock the shield in its extended position. In the first place, the likelihood of unintentional and irreversible locking is greater with such devices than with those devices which require rotation to lock. Also, it is difficult to verify that the shield is locked upon such forcible extension without attempting to retract the shield, which increases the possibility of unintended exposure of the needle. Further some of the safety syringes currently available allow the shield to be pulled axially from the syringe with only moderate applied force and or to be removed with moderate wiggling which has been attributed to the use of relatively soft polymers in combination with relatively small protrusions as the engaging elements of the shield and/or other components of the safety syringe. Finally, if the user's hand should slip from the shield while exerting the force necessary to extend the shield to the locked position, the user's hand may reflexively rebound back onto the needle point if the shield does not actually lock.

Accordingly, it is an object of this disclosure to provide a protective shield of the type described which provides a relatively inexpensive protective shield which satisfies the functional requirements of a needle shield and includes none of the drawbacks mentioned above.

Another object is to provide an extendable needle shield for a syringe which performs all of the necessary functions of such a shield and which is particularly well suited to an automated process of manufacture.

A further object of the disclosure is to provide an extendable needle shield for a safety syringe which is improved from the points of view of safety, functional utility, and cost of manufacture.

SUMMARY

This disclosure pertains to a safety syringe comprising: a barrel having a distal and proximal ends; a plunger sealingly slidable within the barrel; a collar having proximal and distal ends; a hollow needle attached to the distal end of the barrel; and an elongate generally tubular needle shield moveable over the barrel, said elongate generally tubular needle shield having a proximal end, a distal end, a lumen therebetween, and a longitudinal axis, wherein the hollow needle is attached to the barrel via a generally tubular needle hub integrally formed with the distal end of the barrel, said generally tubular needle hub having disposed about its external surface a plurality of ribs adapted to join the collar to the generally tubular needle hub; wherein each rib of the plurality of ribs includes an at least partially relieved proximal region to provide a region adapted to be readily frangible when the elongate generally tubular needle shield is positioned distal of the barrel and subjected to a lateral force applied thereto distal of the barrel; further wherein the collar is adapted to be slidably received within the elongate generally tubular needle shield and to be prevented from being withdrawn proximally therefrom.

The disclosure also pertains to a method of using a safety syringe comprising: positioning an elongate generally tubular needle shield relative to a barrel of a safety syringe such that the elongate generally tubular needle shield at least partially covers the barrel and such that at least a portion of a hollow needle associated with the safety syringe extends distal of the elongate generally tubular needle shield; inserting the hollow needle of the safety syringe into a quantity of a fluid to be dispensed; withdrawing a plunger slidable within the barrel, thereby filling the syringe with fluid to be dispensed; removing the hollow needle of the safety syringe from the fluid to be dispensed; ejecting the fluid to be dispensed; positioning the elongate generally tubular needle shield distal of the barrel thereby covering the hollow needle associated with the safety syringe with the elongate generally tubular needle shield; grasping the barrel of the safety syringe thereby substantially preventing transverse motion; and applying a force to the elongate generally tubular needle shield in a direction perpendicular to a longitudinal axis of the elongate generally tubular needle shield sufficient to break an at least partially relieved proximal region between the syringe barrel and a generally tubular needle hub which attaches the hollow needle associated with the safety syringe to the barrel, said at least partially relieved proximal region being adapted to break upon the application of a perpendicularly applied force.

DETAILED DESCRIPTION

Figure 1:
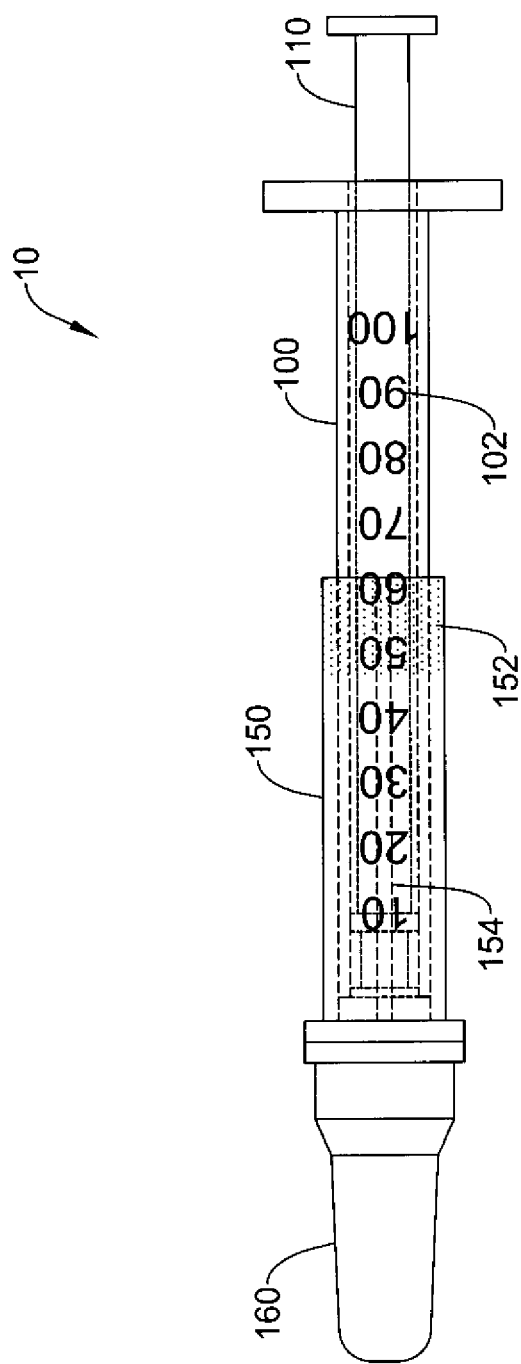
FIG. 1 illustrates an embodiment of a safety syringe of the disclosure.

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary.

FIG. 1, illustrates a non-limiting exemplary embodiment of a safety syringe of the disclosure. The safety syringe 10 includes a syringe body or barrel 100, typically including a graduated scale 102 thereon; a plunger 110 sealingly slidable within the barrel 100; a hollow needle (not shown in this figure); an elongate generally tubular needle shield 150 moveable over the barrel 100; and a distal cap 160 adapted to engage the distal end of the elongate generally tubular needle shield 150. Distal cap 160, if present, includes an internal cavity of sufficient depth to accommodate that portion of the hollow needle (not shown) which extends distally from a generally tubular needle hub to be described herein. Distal cap 160 may have a closed distal end. The barrel 100 and elongate generally tubular needle shield 150 are typically sufficiently translucent or transparent to permit the plunger 110 and a scale 102 printed on the barrel to be seen through the elongate generally tubular needle shield.

Although the elongate generally tubular needle shield 150 of FIG. 1 is depicted as having a circular cross-section, it will be appreciated that the function may be provided by elongate generally tubular needle shields having other cross-sectional shapes such as a triangle, a rectangle, a higher polygon, an oval, or the like. In some embodiments, the elongate generally tubular needle shield may have a cross-section which is somewhat elongated along a transverse axis to provide a better gripping surface for translation and/or rotation of the elongate generally tubular needle shield relative to the barrel. In other embodiments, an improved gripping surface may be provided by wings or other flanges extending from the surface of the elongate generally tubular needle shield. In yet other embodiments, the elongate generally tubular needle shield 150 may include, on at least a portion of its outer surface, a textured region 152 adapted to provide an improved finger grip. In certain embodiments, the elongate generally tubular needle shield 150 may include a cooperating key or keyway 154 adapted to guide translation of the elongate generally tubular needle shield relative to other components of the safety syringe, while limiting relative rotation except at selected places along the translation path. Complementary key or keyway 154 may include structures (not shown) which cooperate with collar 120 to provide one or more detents to position and/or lock elongate generally tubular needle shield 150 relative to barrel 100. The structure of the detents, if present, is not critical and may be provided by structures known in the art such as mutually engaging protrusions and recesses. Some such engagements may be reversible while others may be irreversible.

Figure 2:
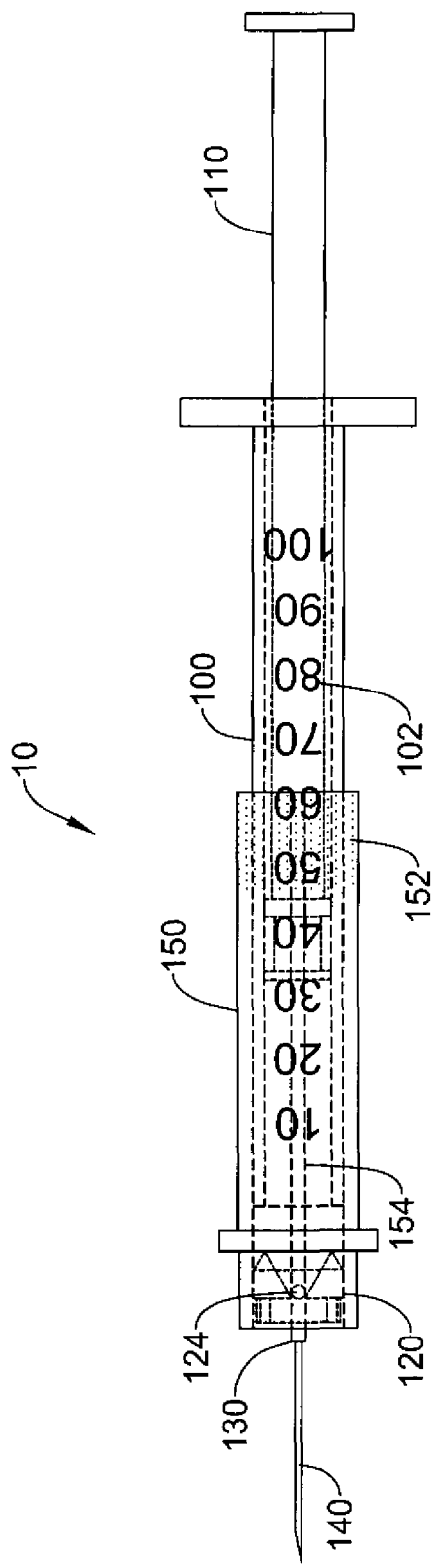
FIG. 2 illustrates the safety syringe embodiment of FIG. 1 with a portion removed.
Figure 3:
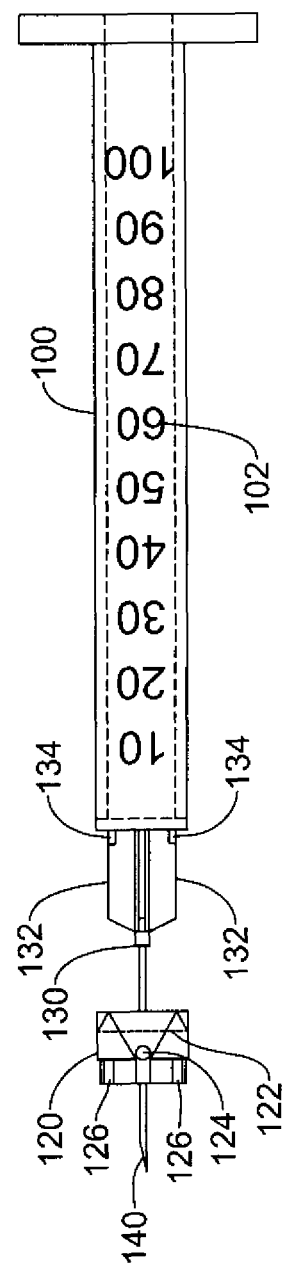
FIG. 3 illustrates a detail of the embodiment of FIG. 1 prior to final assembly.
Figure 4:
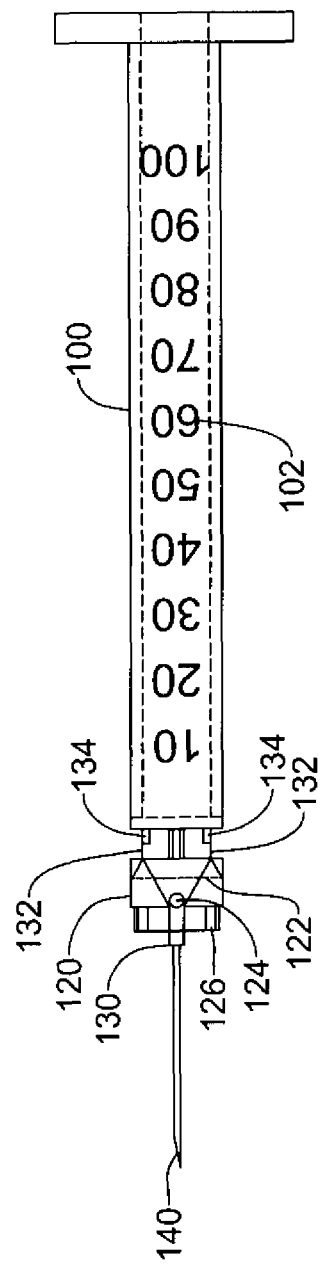
FIG. 4 illustrates the detail of FIG. 3 following assembly.

In FIG. 2, the distal cap 160 has been removed in preparation for use which may better illustrate additional structures associated with the safety syringe 10. Hollow needle 140 may be seen extending distally from generally tubular needle hub 130 to which it may be fixedly attached. In this embodiment, generally tubular needle hub 130 is integrally formed with barrel 100. Generally tubular needle hub 130, better seen in FIGS. 3 and 4, is joined to collar 120 via a plurality of ribs 132 which is integrally formed with the generally tubular needle hub 130. Each rib of the plurality of ribs 132 includes an at least partially relieved proximal region 134 to provide a region adapted to be readily frangible when the elongate generally tubular needle shield 150 is positioned distal of the barrel 100 and subjected to a lateral force applied thereto at a point distal of barrel 100.

In some embodiments, ribs 132, adapted to join the collar 120 to generally tubular needle hub 130, may be deformable and adapted to engage a circumferential inner ridge 122 of collar 120 such that the collar 120 is firmly attached to the plurality of ribs 132 distal of the at least partially relieved proximal region 134 of the plurality of ribs 132. In other embodiments, the plurality of ribs 132, adapted to join the collar 120 to the generally tubular needle hub 130, is fixedly attached to the generally tubular needle hub 130 and by adhesive to the collar 120 distal of the at least partially relieved proximal region 134 of the plurality of ribs 132. In yet other embodiments, the plurality of ribs 132, adapted to join the collar 120 to the generally tubular needle hub 130, is fixedly attached to the generally tubular needle hub 130 and by welding to the collar 120 distal of the at least partially relieved proximal region 134 of the plurality of ribs 132. It will be appreciated that those deformable ribs 132, adapted to engage a circumferential inner ridge 122 of collar 120, may additionally be fixedly attached to the collar by adhesive or welding if desired. In still other embodiments, barrel 100, collar 120, generally tubular needle hub 130, and the plurality of ribs 132, each including a relieved proximal region 134, may be integrally formed. These fixation methods may significantly increase the force required to remove elongate generally tubular needle shield 150 from the remaining components of safety syringe 10 by pulling and/or wiggling the elongate generally tubular needle shield 150 relative to the syringe barrel 100. In each of the above embodiments, the plurality of ribs 132 may include two, three, four, or more ribs 132.

FIG. 3 illustrates a barrel 100, generally tubular needle hub 130, ribs 132 with at least partially relieved proximal regions 134, and a hollow needle 140 prior to assembly with collar 120 having an inner circumferential ridge 122. FIG. 4 illustrates the components after assembly in partial detail such that the at least partially relieved proximal region 134 may be seen. Elongate generally tubular needle shield 150 has been omitted from these figures for clarity. Depending upon details of the elongate generally tubular needle shield 150 and collar 120, which details should not be viewed as limiting in the current disclosure, safety syringe 10 may be assembled by inserting generally tubular needle hub 130 into the proximal end of elongate generally tubular needle shield 150 and advancing generally tubular needle hub 130 until hollow needle 140 extends distally from the elongate generally tubular needle shield 150. Collar 120 may then be pressed over deformable ribs 132 to engage circumferential inner ridge 122 of collar 120 thereby firmly attaching collar 120 to generally tubular needle hub 130 via the plurality of deformable ribs 132. If desired, ribs 132 may be fixedly attached to collar 120 as discussed above. In such assemblies, the proximal end of elongate generally tubular needle shield 150 may include one or more projections adapted to prevent collar 120 from being withdrawn proximally through the proximal end of generally tubular needle shield 150.

Figure 5:
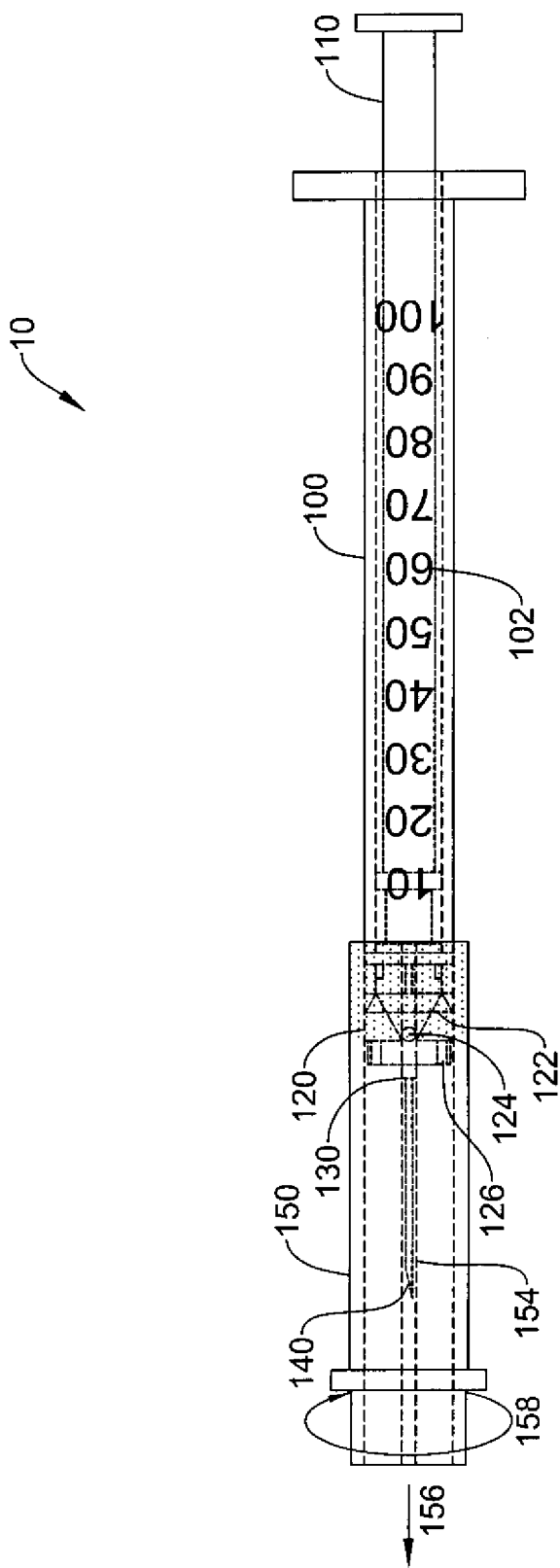
FIG. 5 illustrates one of the configurations of the safety syringe embodiment of FIG. 1.

FIGS. 5, 5A, 5B, and 6 illustrate the use of safety syringe 10, following the administration of a drug or other fluid. As illustrated, the safety syringe 10 may be operated with a single hand for convenience; however two hands may be used depending on operator preference. In FIG. 5, the elongate generally tubular needle shield 150 has been advanced distally along keyway 154. If an optional detent 124 is present, detent 124 may be engaged by urging the elongate generally tubular needle shield 150 distally with respect to the barrel as shown by the arrow 156. In some embodiments, detent 124 may also hold elongate generally tubular needle shield 150 in a proximally retracted position during use. If a second optional detent 126 is present, the second detent may be engaged by rotating the elongate generally tubular needle shield 150 relative to the barrel, as shown by curved arrow 158, thereby locking the collar 120 and generally tubular needle hub 130 near the proximal end of the elongate generally tubular needle shield 150.

Figure 5A:
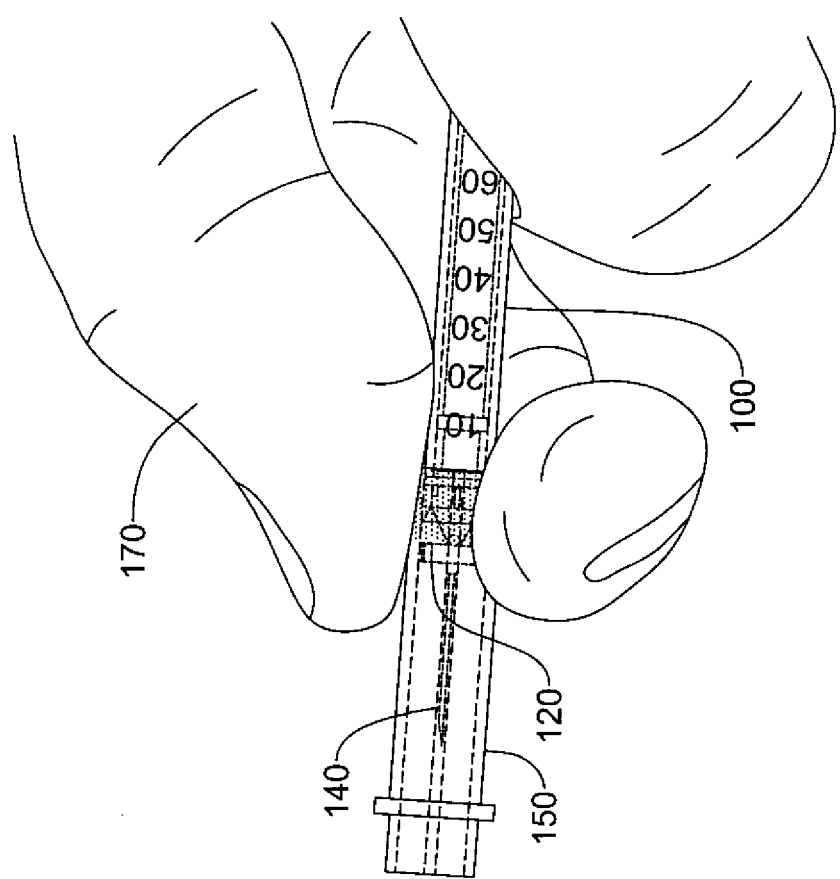
FIG. 5A illustrates one of the optional steps in the use of a safety syringe embodiment of FIG. 1.
Figure 5B:
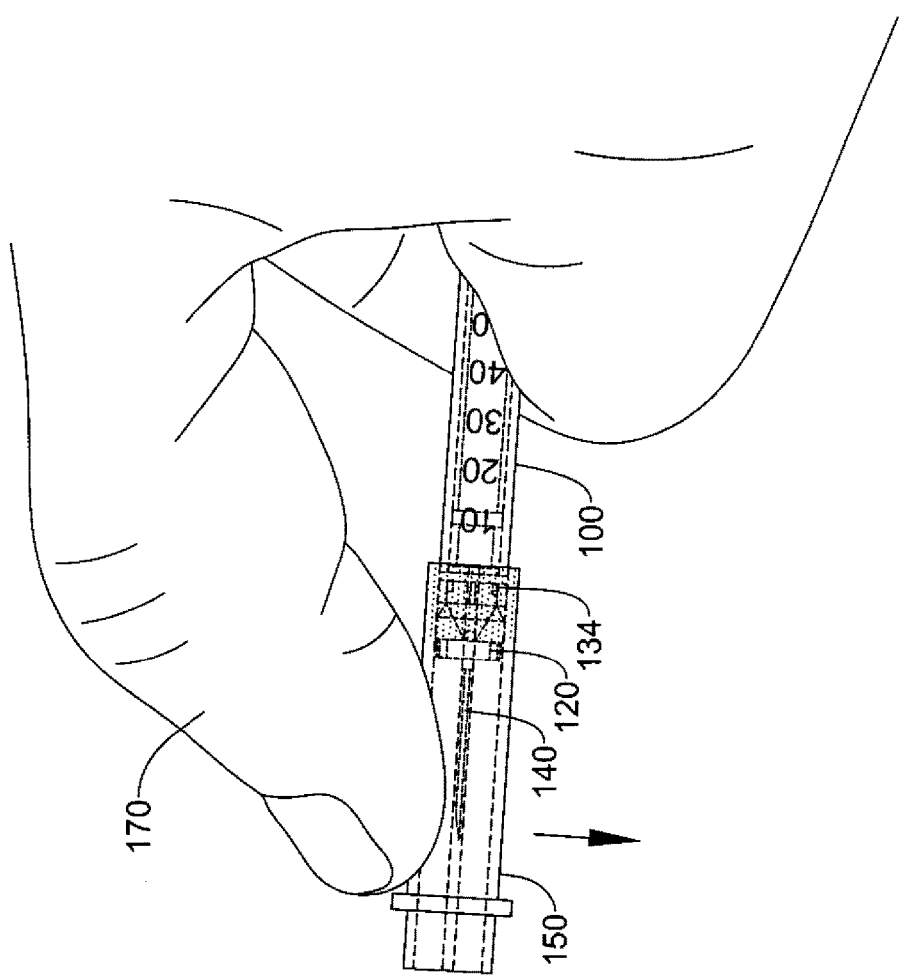
FIG. 5B illustrates one of the optional steps in the use of a safety syringe embodiment of FIG. 1.
Figure 6:
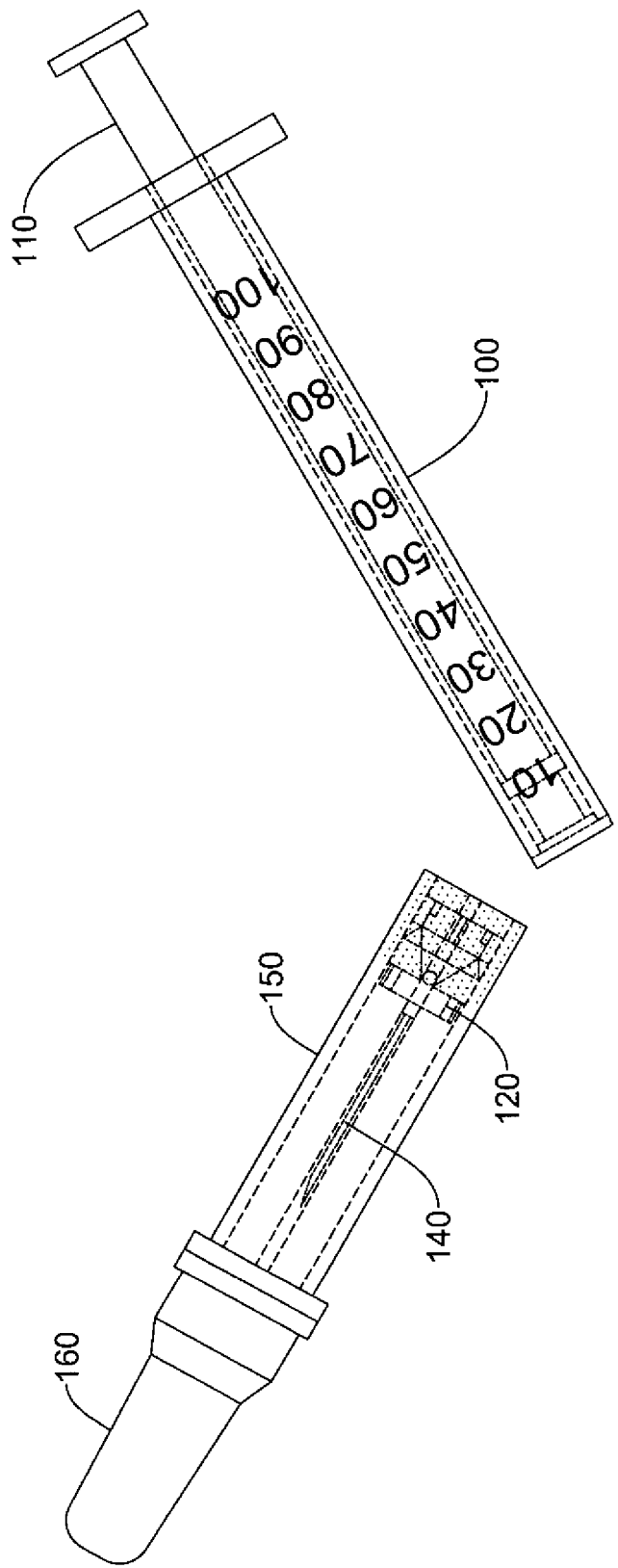
FIG. 6 illustrates a safety syringe embodiment of FIG. 1 prepared for disposal.

In FIG. 5A, operator 170 has used a thumb and forefinger of one hand to slide elongate generally tubular needle shield 150 distally with respect to barrel 100, held by the remaining fingers, thereby optionally engaging a detent (not visible in this view) and further has rotated elongate generally tubular needle shield 150 to lock elongate generally tubular needle shield 150 to collar 120 via a second optional detent (not visible in this view). In FIG. 5B, operator 170 has started to apply a force, perpendicular to the barrel 100, to elongate generally tubular needle shield 150, which is being held by the remaining fingers. Further application of force will cause generally tubular needle hub 130 and plurality of ribs 132 to break at the at least partially relieved region 134 allowing separate disposal of the protected used needle 140 and the barrel 100/plunger 110 of the syringe as shown in FIG. 6. Separate disposal of the barrel 100/plunger 110 of the syringe allows recycling of those parts thereby reducing the volume of medical waste.

In use, elongate generally tubular needle shield 150 is initially retracted proximally relative to the barrel 100 to expose the tip and a portion of the shaft of hollow needle 140 and typically a portion of generally tubular needle hub 130. In some embodiments, the elongate generally tubular needle shield 150 may be releasably held in the retracted position by cooperation between optional detent components associated with elongate generally tubular needle shield 150 and collar 120. Plunger 110 is advanced fully distally. Hollow needle 140 may then be inserted into a fluid to be dispensed, often by passing the tip of hollow needle 140 through the septum of a vial containing a drug or other fluid to be dispensed. Withdrawing plunger 110 relative to barrel 100 causes fluid to be drawn through hollow needle 140 to fill a portion of the barrel with the fluid to be dispensed. The amount of fluid contained within the barrel may be determined by reference to scale 102 in the conventional manner. Scale 102 on barrel 100 as well as plunger 110 can be viewed through translucent or transparent elongate generally tubular needle shield 150.

Once the fluid has been delivered to the desired site through needle 140 by moving plunger 110 distally, the elongate generally tubular needle shield 150 may be advanced distally over barrel 100 to a stop or optional detent thereby covering hollow needle 140. This may be accomplished as a single-handed operation if desired. In some embodiments, the combination of elongate generally tubular needle shield 150 and collar 120 may also include a second detent capable of being engaged by rotating the elongate generally tubular needle shield 150 relative to barrel 100 thereby locking the collar 120 proximate the proximal end of the elongate generally tubular needle shield 150. The optional locking operation also may be accomplished with one hand if desired. See FIGS. 5 and 5A.

With elongate generally tubular needle shield 150 advanced distally and optionally locked to collar 120, the operator may then apply a force in a direction perpendicular to the longitudinal axis of the elongate generally tubular needle shield 150 sufficient to break the safety syringe at the at least partially relieved proximal region between barrel 100 and elongate generally tubular needle shield 150, thereby separating the used hollow needle 140 component from the barrel 100/plunger 110 component to allow separate disposal of the respective components in an approved medical waste container. For an added measure of protection, cap 160 may be reinstalled. Operator 170 may separate the used hollow needle 140 component from the barrel 100/plunger 110 component with a single hand, if desired, by grasping the barrel 100 with the fingers while pressing laterally on the elongate generally tubular needle shield 150 distal of the barrel 100 as illustrated in FIG. 5B.

Although the illustrative examples described above relate to a specific exemplary embodiment of a single use safety syringe, use with other safety syringes is also contemplated. In such embodiments, details of elements corresponding to the collar, elongate generally tubular needle shield, and ribs may be modified while preserving the enhanced ability to break reliably and predictably at a region adjacent to the distal end of the syringe barrel.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. A safety syringe comprising:
   a barrel having a distal end and a proximal end;
   a plunger sealingly slidable within the barrel;
   a collar having proximal and distal ends;
   a hollow needle attached to the distal end of the barrel; and
   an elongate generally tubular needle shield which is moveable over the barrel from a first proximally retracted configuration in which a distal portion of the hollow needle is exposed to a second distally extended configuration in which the hollow needle is fully within the elongate generally tubular needle shield, said elongate generally tubular needle shield having a proximal end, a distal end, a lumen therebetween, and a longitudinal axis,
   wherein the hollow needle is attached to the barrel via a generally tubular needle hub integrally formed with the distal end of the barrel, said generally tubular needle hub having disposed about its external surface a plurality of ribs adapted to join the collar to the generally tubular needle hub;
   wherein each rib of the plurality of ribs includes an at least partially relieved circumferential region;
   further wherein the collar is adapted to be slidably received within the elongate generally tubular needle shield and to be prevented from being withdrawn proximally therefrom.

2. The safety syringe of claim 1, wherein the collar and the elongate generally tubular needle shield cooperate to hold the elongate generally tubular needle shield in a first position wherein the elongate generally tubular needle shield is extended distally with respect to the barrel and the collar is proximate the proximal end of the elongate generally tubular needle shield.

3. The safety syringe of claim 2, further wherein a portion of the collar and a portion of the elongate generally tubular needle shield cooperate to form a detent mechanism adapted to lock the elongate generally tubular needle shield in the second distally extended configuration when the elongate generally tubular needle shield is extended distally with respect to the barrel and the collar is proximate the proximal end of the elongate generally tubular needle shield.

4. The safety syringe of claim 3, wherein the first proximally retracted configuration and the second distally extended configuration of the elongate generally tubular needle shield are related by a rotation of the elongate generally tubular needle shield about the longitudinal axis thereof relative to the collar.

5. The safety syringe of claim 1, wherein at least a portion of the elongate generally tubular needle shield is sufficiently translucent to permit the plunger and a scale printed on the barrel to be seen through the elongate generally tubular needle shield.

6. The safety syringe of claim 1, wherein the elongate generally tubular needle shield includes one of a key or a keyway adapted to slidingly engage a complementary keyway or complementary key respectively associated with the collar.

7. The safety syringe of claim 1, wherein the elongate generally tubular needle shield includes on at least a portion of its outer surface a textured region adapted to provide an improved finger grip.

8. The safety syringe of claim 1, wherein the plurality of ribs disposed about the generally tubular needle hub integrally formed with the distal end of the barrel consists of three ribs.

9. The safety syringe of claim 1, wherein the plurality of ribs disposed about the generally tubular needle hub integrally formed with the distal end of the barrel consists of four ribs.

10. The safety syringe of claim 1, further comprising a cap having a closed distal end and adapted to frictionally engage the distal end of the elongate generally tubular needle shield.

11. The safety syringe of claim 10, wherein the cap includes an internal cavity having sufficient length to accommodate the hollow needle when the elongate generally tubular needle shield is retracted proximally.

12. The safety syringe of claim 1, wherein a portion of the elongate generally tubular needle shield and a portion of the collar cooperate to provide a detent mechanism adapted to reversibly hold the elongate generally tubular needle shield in a third configuration in which the elongate generally tubular needle shield is retracted proximally sufficiently to fully expose a portion of the hollow needle which is disposed distal of the generally tubular needle hub integrally formed with the distal end of the barrel.

13. The safety syringe of claim 1, wherein the plurality of ribs adapted to join the collar to the generally tubular needle hub is also adapted to deformably engage a circumferential inner ridge of the collar such that the collar is attached to the plurality of ribs at a point distal of the at least partially relieved circumferential region of the plurality of ribs.

14. The safety syringe of claim 1, wherein the plurality of ribs adapted to join the collar to the generally tubular needle hub is fixedly attached by adhesive to the collar at a point distal of the at least partially relieved circumferential region of the plurality of ribs.

15. The safety syringe of claim 1, wherein the plurality of ribs adapted to join the collar to the generally tubular needle hub is fixedly attached by welding to the collar at a point distal of the at least partially relieved circumferential region of the plurality of ribs.

16. The safety syringe of claim 1, wherein the barrel, the collar, the generally tubular needle hub and the plurality of ribs each including at least a partially relieved circumferential region are integrally formed.

17. The safety syringe of claim 1, wherein the at least partially relieved circumferential region is adapted to be readily frangible when the elongate generally tubular needle shield is positioned distal of the barrel and subjected to a lateral force applied thereto distal of the barrel.

* * * * *